US012760208B2

(12) United States Patent
Laferte et al.

(10) Patent No.: US 12,760,208 B2

(45) Date of Patent: Oct. 13, 2026

(54) HOT MELT ADHESIVE COMPOSITION

(71) Applicant: BOSTIK SA, Colombes (FR)

(72) Inventors: Olivier Laferte, Venette (FR); Laurianne Libralesso, Venette (FR); Stéphanie Komar, Venette (FR); Clement Bellini, Venette (FR); Jian Ping Shi, Shanghai (CN); Danfeng Li, Shanghai (CN)

(73) Assignee: BOSTIK SA, Puteaux (FR)

( * ) Notice: Subject to any disclaimer, the term of this patent is extended or adjusted under 35 U.S.C. 154(b) by 175 days.

(21) Appl. No.: 18/042,468

(22) PCT Filed: Aug. 25, 2021

(86) PCT No.: PCT/EP2021/073515

§ 371 (c)(1),
(2) Date: Feb. 22, 2023

(87) PCT Pub. No.: WO2022/043382

PCT Pub. Date: Mar. 3, 2022

(65) Prior Publication Data

US 2023/0323167 A1 Oct. 12, 2023

(30) Foreign Application Priority Data

Aug. 26, 2020 (EP) .................................... 20305951
Sep. 24, 2020 (EP) .................................... 20306087

(51) Int. Cl.

*C09J 7/35* (2018.01)
*A61L 15/58* (2006.01)
*C09J 7/21* (2018.01)
*C09J 153/02* (2006.01)

(52) U.S. Cl.

CPC .......... *C09J 153/02* (2013.01); *A61L 15/585* (2013.01); *C09J 7/21* (2018.01); *C09J 7/35* (2018.01)

(58) Field of Classification Search

CPC .... C09J 153/02; C09J 7/21; C09J 7/35; A61L 15/585; A61F 13/472

See application file for complete search history.

(56) References Cited

U.S. PATENT DOCUMENTS 4,246,221 A 1/1981 Mccorsley, III
5,869,562 A † 2/1999 Lindquist
9,879,160 B2 * 1/2018 Schroeyers ............ C09J 123/14
2005/0013996 A1 * 1/2005 Hatfield ..................... C09J 5/00 524/505
2006/0229411 A1 10/2006 Hatfield et al.
2008/0020203 A1 1/2008 Tabata
2009/0264580 A1 * 10/2009 Abba .................... A61L 15/585 524/505
2010/0248572 A1 9/2010 Firgo et al.
2011/0104487 A1 * 5/2011 Schroeyers ............ C09J 123/10 524/505
2013/0130027 A1 * 5/2013 Curry ...................... C09J 123/14 524/505
2015/0038936 A1 * 2/2015 Austin .................. A61L 15/225 604/387
2015/0203725 A1 7/2015 Stafeil et al.
2019/0106601 A1 4/2019 Hanle et al.

FOREIGN PATENT DOCUMENTS

EP 2066758 B1 * 6/2012 ........ C09J 123/0815
EP 3098242 * 11/2016
EP 3098242 A1 11/2016
EP 3144363 A1 3/2017
EP 3433330 A1 1/2019
EP 3842504 A1 * 6/2021 ............ C06J 153/02
JP H 09208919 * 8/1997
JP H09208919 A 8/1997
JP 2012207127 A 10/2012
JP 2013067782 A 4/2013
WO 2006070529 A1 7/2006
WO 2009036481 A1 3/2009
WO 2010143653 A1 12/2010
WO 2016181769 A1 11/2016
WO 2017162737 A1 9/2017
WO 2018104330 A1 6/2018
WO 2020040175 A1 2/2020
WO WO2020/040175 * 2/2020
WO WO-2020121278 A1 * 6/2020 ............... B65B 7/16

OTHER PUBLICATIONS

The Kraton Polymers and Compounds Product Application Guide, 2010.*

ISA/EP; International Search Report and Written Opinion for International Patent Application No. PCT/EP2021/073515 dated Jan. 7, 2022, 8 pages.

"Kraton, Polymers and Compounds Product and Application Guide," pp. 1-20, 2010, Kraton Polymers, LLC.†

* cited by examiner
† cited by third party

*Primary Examiner* — Kumar R Bhushan

(74) *Attorney, Agent, or Firm* — Rimon P.C.; Allyn B. Elliott

(57) ABSTRACT

The present invention relates to a pressure sensitive hot melt adhesive, particularly to a pressure sensitive hot melt positioning adhesive for use on feminine sanitary pads or adult incontinent products having improved peel values on fabrics made from Lyocell fibers, particularly eucalyptus-based Lyocell fibers.

12 Claims, No Drawings

HOT MELT ADHESIVE COMPOSITION

CROSS-REFERENCE TO RELATED APPLICATIONS

This application is a U.S. National Stage application of International Patent Application No. PCT/EP2021/073515, filed on Aug. 25, 2021, which claims the benefit of European Patent Application No. 20306087.6, filed on Sep. 24, 2020, and the benefit of European Patent Application No. 20305951.4, filed on Aug. 26, 2020.

TECHNICAL FIELD

The present invention relates to a pressure sensitive hot melt adhesive, particularly to a pressure sensitive hot melt positioning adhesive for use on feminine sanitary pads or adult incontinent products having improved peel values on fabrics made from Lyocell fibers, particularly eucalyptus-based Lyocell fibers.

TECHNICAL BACKGROUND

Hot melt adhesives have been used for many years in the construction of a wide variety of disposable nonwoven goods, such as disposable diapers, training pants, adult incontinent products (pads or briefs), feminine care products (napkins or pads) and surgical masks. These items aim at receiving and containing body fluids and are usually worn against or in close proximity to the skin. One specific application where pressure sensitive hot melts have traditionally been used is to adhere a feminine care article to a woman's undergarment. This requires a precise balance of adhesion properties to ensure the article is adhered so that its stays in place during use but is also capable of being removed without leaving residue on or damaging the undergarment. Historically, these pressure sensitive hot melt adhesives have been formulated using styrene block copolymers.

Today's undergarment market, like many other industries, is experiencing significant changes in both materials and design. Traditionally, many of the undergarments were manufactured utilizing fabrics that demonstrate similar characteristics across different regions of the world, such as natural cotton, synthetic nylon and polyester. Undergarments were also manufactured utilizing fabrics being more regionally specific, such as other synthetic fabrics having specific characteristics and properties, being surface-treated, etc. In order to further increase the user's expectation, acceptance and comfort, there is still the need for providing undergarments utilizing alternative fabrics. For example, undergarments manufactured from Lyocell fibers, particularly from eucalyptus based Lyocell fibers, have recently been commercialized. Suitable processes for producing Lyocell fibers are described for example in the U.S. Pat. No. 4,246,221 published on 20 Jan. 1981, the PCT application WO 2018/104330 A1 published on 14 Jun. 2018 and the PCT application WO 2009/036481 A1 published on 26 published March 2009, which are incorporated herewith by reference. Lyocell fabrics are made from cellulose and are environmentally friendly, tough, hypoallergenic, breathable, and they keep the undergarment drier.

Hot melt adhesive compositions are known in various applications. Indeed, Document WO 2010/143653 A1 relates to a rolled medical adhesive tape, and more particularly to a pressure-sensitive adhesive tape for medical use which has a nonwoven fabric excellent in air permeability and stretchability as a support and which is directly wound without intervention of a release liner. Document JP 2013067782 relates to an optical adhesive comprising an adhesive resin having a weight-average molecular weight of 200,000 to 2,000,000, a pigment, a dispersant and a curing agent and comprising an adhesive agent layer formed of the optical adhesive. Document EP 3433330 A1 relates to an adhesive tape made from preferably a textile support and from an adhesive mass which is in the form of a dried polymer dispersion and which is applied to at least one side of the support. The polymer is made from 95 to 100 wt % n-butylacrylate and/or 2-ethylhexylacrylate, and 0 to 5 wt % ethylenically unsaturated monomer having an acid or acid anhydride function. Document EP 3144363 A1 relates to a wood adhesive comprising a first agent and a second agent. The first agent includes a sodium carboxymethyl cellulose and a styrene-butadiene rubber polymer, while the second agent comprises a polymeric quaternary amine. Document US 2006/0229411 A1 relates to a hot melt pressure sensitive adhesive formulated without the used of isoprene-containing polymers using a combination of different styrene/butadiene copolymers including at least one SBS triblock copolymer. Document US 2015/0203725 A1 relates to a hot melt adhesive composition, particularly for use on feminine sanitary pads or adult incontinent products, comprising a first styrene block copolymer comprising, amongst other compounds, a styrene-butadiene-styrene block polymer with a styrene content greater than 30% by weight and a diblock content greater than 30% by weight, and a second styrene block copolymer which can have either an isoprene or butadiene midblock with a lower diblock content than the first styrene block copolymer.

Even though, known hot melt adhesives present a good adhesion on different types of fabrics, the adhesion is not satisfactory on man-made fibers such as Lyocell fibers, particularly on eucalyptus based Lyocell fibers, as there is an important loss of peel performance.

There is thus a need for a hot melt adhesive composition suitable for hygiene disposable articles, which provides good adhesion, in a variety of materials and fabrics. More particularly, there is a need for a hot melt adhesive composition which provides good adhesion of hygiene disposable articles on fabrics made from Lyocell fibers, particularly from eucalyptus based Lyocell fibers.

SUMMARY OF THE INVENTION

It is a first object of the invention to provide a hot melt adhesive composition comprising, by total weight of the composition: from 5 to 35% by weight of at least one styrene block polymeric component having an average hardness Shore A of 60 or less, preferably from 15 to 60, more preferably from 20 to 60; from 40 to 65% by weight of at least one tackifying resin; from 15 to 40% by weight at least one plasticizer; and from 0 to 5% by weight of at least one stabilizer.

In some embodiments, the at least one stabilizer is in an amount of from 0 to 3% by weight, the hot melt adhesive composition further comprising from 0 to 5% of at least one additive, by total weight of the composition.

In some embodiments, the polymeric component comprises, by total weight of the polymeric component: from 25 to 100% by weight of at least one linear styrene block copolymer (a) having a styrene block content of 21% or less and a hardness Shore A of 45 or less; from 0 to 75% by weight of at least one linear styrene block copolymer (b) having a styrene block content from 22% to about 45%.

In some embodiments, the polymeric component comprises, by total weight of the polymeric component, from 35 to 100% of copolymer (a) and from 0 to 65% of copolymer (b); preferably from 45 to 100% of copolymer (a) and from 0 to 55% of copolymer (b).

In some embodiments, the polymeric component comprises, by total weight of the polymeric component, from 25 to 95% of copolymer (a) and from 5 to 75% of copolymer (b); preferably from 35 to 90% of copolymer (a) and from 10 to 65% of copolymer (b); more preferably from 45 to 85% of copolymer (a) and from 15 to 55% of copolymer (b).

In some embodiments, the polymeric component consists of at least one copolymer (a).

In some embodiments, the copolymer (a) is chosen from the group consisting of SB, SI, SEB, SEP, SBBS, SBS, SEBS, SEPS, SEEPS, SIBS, SIS, random-block SBR, random-block SIR, and mixtures thereof; preferably from the group consisting of SBBS, SBS, SEBS, SEPS, SEEPS, SIBS, SIS, random-block SBR, random-block SIR and mixtures thereof; more preferably from the group consisting of SIS, random-block SBR and mixtures thereof.

In some embodiments, the copolymer (a) is chosen from the group consisting of SB, SI, SEB, SEP, SBBS, SBS, SEBS, SEPS, SEEPS, SIBS, SIS, random-block SBR, random-block SIR, and mixtures thereof; preferably from the group consisting of SBBS, SBS, SEBS, SEPS, SEEPS, SIBS, SIS, random-block SBR, random-block SIR and mixtures thereof; more preferably from the group consisting of SIS, random-block SBR, SEBS and mixtures thereof.

In some embodiments, the copolymer (b) is chosen from the group consisting of SB, SI, SEB, SEP, SBBS, SBS, SEBS, SEPS, SEEPS, SIBS, SIS, random-block SBR, random-block SIR and mixtures thereof; preferably from SBBS, SBS, SEBS, SEPS, SEEPS, SIBS, SIS, random-block SBR, random-block SIR and mixtures thereof; more preferably from the group consisting of SIS, SBS, SEBS and mixtures thereof.

In some embodiments, the polymeric composition is chosen from the group consisting of: from 60 to 70% of random-block SBR copolymer (a) and from 30 to 40% of SIS copolymer (b); from 75 to 85% of random-block SBR copolymer (a) and from 15 to 25% of SIS copolymer (b); from 30 to 40% of random-block SBR copolymer (a) and from 60 to 70% of SIS copolymer (b); from 45 to 55% of random-block SBR copolymer (a) and 45 to 55% of SIS copolymer (b); from 20 to 30% of random-block SBR copolymer (a) and from 70 to 80% of SIS copolymer (b); from 60 to 70% of random-block SBR copolymer (a) and from 30 to 40% of SEBS copolymer (b); from 60 to 70% of SIS copolymer (a) and from 30 to 40% of SIS copolymer (b); from 60 to 70% of SIS copolymer (a) and from 30 to 40% of SEBS copolymer (b); from 100% of SIS copolymer (a); from 100% of random-block SBR polymer (a); from 100% of a composition of copolymers (a) consisting of 60 to 70% of SIS copolymer (a) and from 30 to 40% of random-block SBR copolymer (a); from 100% of a composition of copolymers (a) consisting of 45 to 55% of SIS copolymer (a) and from 45 to 55% of random-block SBR copolymer (a); from 27 to 37% of random-block SBR copolymer (a), from 27 to 37% of SIS copolymer (b) and from 30 to 40 of SEBS copolymer (b); from 30 to 40% of SIS copolymer (a), from 17 to 27% of SEBS copolymer (a) and from 38 to 48% of SIS copolymer (b).

In some embodiments, the composition has a Brookfield viscosity at 163° C. from 500 to 8,000 mPa·s, preferably from 500 to 4,000 mPa·s, more preferably from 800 to 3,000 MPa·s.

It is a second object of the invention to provide a use of the hot melt adhesive composition for adhering a hygiene disposable article on a fabric.

In some embodiments, the hygiene disposable article is chosen from nonwoven hygiene disposable articles; preferably from the group consisting of adult incontinent products and feminine care products.

In some embodiments, the fabric is manufactured utilizing natural or synthetic fibers; preferably cotton, nylon, polyester, other man-made fibers and mixtures thereof; more preferably Lyocell fibers; still more preferably eucalyptus based Lyocell fibers.

The present invention makes it possible to address the needs mentioned above. In particular, the invention provides a pressure sensitive hot melt adhesive composition which provides good adhesion to hygiene disposable articles on a variety of materials and fabrics. In addition, the present invention makes it possible to provide a hot melt adhesive composition which provides good adhesion to hygiene disposable articles on any suitable fabrics, including fabrics obtained from man-made fibers such as Lyocell fibers, particularly from eucalyptus based Lyocell fibers. In particular, it has been surprisingly found that a pressure sensitive hot melt adhesive composition according to the present invention makes it possible to adhere hygiene disposable articles on fabrics made from man-made fibers, such as eucalyptus-based Lyocell fibers with an improved peel performance.

DESCRIPTION OF EMBODIMENTS

The invention will now be described in more detail without limitation in the following description.

Definitions

The term "hot melt" is used herein to describe that the adhesive composition requires to be heated at least at 120° C., preferably at least at 140° C., to be applied on a substrate. The hot melt adhesive composition is thus solid at 23° C.

By "SBBS" is meant a styrene-butadiene-butylene-styrene triblock copolymer.

By "SBS" is meant a styrene-butadiene-styrene triblock copolymer.

By "SEBS" is meant a styrene-ethylene-butylene-styrene triblock copolymer.

By "SEPS" is meant a styrene-ethylene-propylene-styrene triblock copolymer.

By "SEEPS" is meant a styrene-ethylene-ethylene-propylene-styrene triblock copolymer.

By "SIBS" is meant a styrene-isoprene-butadiene-styrene triblock copolymer.

By "SIS" is meant a styrene-isoprene-styrene triblock copolymer.

By "SBC" is meant a copolymer comprising at least one styrene block, including styrene triblock copolymers and styrene diblock copolymers.

By "random-block SBR" is meant random-block styrene butadiene copolymers (part of the styrene being present as polystyrene blocks).

By "random-block SIR" is meant random-block isoprene butadiene copolymers (part of the styrene being present as polystyrene blocks).

By "SB" is meant a styrene-butadiene diblock copolymer.

By "SI" is meant a styrene-isoprene diblock copolymer.

By "SEB" is meant a styrene-ethylene-butylene diblock copolymer.

By "SEP" is meant a styrene-ethylene-propylene diblock copolymer.

By "diblock content" is meant the weight proportion of diblock copolymers in a polymer component.

Hot Melt Adhesive Composition

In a first aspect, the present invention relates to a hot melt adhesive composition comprising, by total weight of the composition:

- from 5 to 35% by weight of at least one styrene block polymeric component having an average hardness Shore A of 60 or less, preferably from 15 to 60, more preferably from 20 to 60;
- from 40 to 65% by weight of at least one tackifying resin;
- from 15 to 40% by weight of at least one plasticizer; and
- from 0 to 5% by weight of at least one stabilizer.

Advantageously, the hot melt adhesive composition may comprise, by total weight of the composition:

- from 5 to 35% by weight of at least one styrene block polymeric component having an average hardness Shore A of 60 or less, preferably from 15 to 60, more preferably from 20 to 60;
- from 40 to 65% by weight of at least one tackifying resin;
- from 15 to 40% by weight of at least one plasticizer;
- from 0 to 3% by weight of at least one stabilizer; and
- from 0 to 5% by weight of at least one additive.

The Styrene Block Polymeric Component

The hot melt adhesive composition comprises a styrene block polymeric component having an average hardness Shore A of about 60 or less, preferably from about 15 to about 60, more preferably from about 20 to about 60. By "styrene block polymeric component" is meant a component consisting of at least one SBC i.e. a copolymer comprising at least one styrene block, including styrene triblock copolymers and styrene diblock copolymers. The terms "styrene block polymeric component" and "polymeric component" are used interchangeably. The average hardness Shore A of the polymeric component is calculated from the hardness Shore A of the styrene block copolymers forming the polymeric component as follows: the sum of [the hardness Shore A of each copolymer multiplied by its weight proportion in the polymeric component], divided by 100. For example, the average hardness Shore A may be of about 55 or less; or of about 50 or less; or of about 45 or less; or of about 40 or less; or of about 35 or less; or of about 30 or less.

In a preferred embodiment, the hot melt adhesive composition comprises, by total weight of the composition:

- from 5 to 35% by weight of at least one styrene block polymeric component having an average hardness Shore A of 50 or less, more preferably of 45 or less; and even more preferably of 40 or less;
- from 40 to 65% by weight of at least one tackifying resin;
- from 15 to 40% by weight at least one plasticizer; and
- from 0 to 5% by weight of at least one stabilizer.

The hot melt adhesive composition comprises from about 5 to about 35%, preferably from about 10 to about 30%, more preferably from about 15 to about 25%, of polymeric component, by total weight of the composition.

The polymeric component may comprise, by total weight of the polymeric component:

- from about 25 to about 100% by weight of at least one linear styrene block copolymer (a) having a styrene block content of about 21% or less and a hardness Shore A of about 45 or less;
- from about 0 to about 75% by weight of at least one linear styrene block copolymer (b) having a styrene block content from about 22% to about 45%.

The polymeric component may comprise, by total weight of the polymeric component:

- from about 25 to about 100% by weight of at least one linear styrene block copolymer (a) having a styrene block content of about 21% or less and a hardness Shore A of about 50 or less;
- from about 0 to about 75% by weight of at least one linear styrene block copolymer (b) having a styrene block content from about 22% to about 45%.

In a preferred embodiment, the average molecular weight (Mn) of each of linear styrene block copolymer(s) (a) and linear styrene block copolymer(s) (b) as defined herein, ranges from 70 000 g/mol to 170 000 g/mol.

In one embodiment, the hot melt adhesive composition comprises, by total weight of the composition:

- from 5 to 35% by weight of at least one styrene block polymeric component having an average hardness Shore A of 50 or less, preferably from 15 to 50, more preferably from 20 to 50;
- from 40 to 65% by weight of at least one tackifying resin;
- from 15 to 40% by weight at least one plasticizer; and
- from 0 to 5% by weight of at least one stabilizer.

wherein the polymeric component comprises, by total weight of the polymeric component:

- from 25 to 100% by weight of at least one linear styrene block copolymer (a) having a styrene block content of 21% or less and a hardness Shore A of 45 or less;
- from 0 to 75% by weight of at least one linear styrene block copolymer (b) having a styrene block content from 22% to 45%;

wherein the average molecular weight (Mn) of each of linear styrene block copolymer(s) (a) and linear styrene block copolymer(s) (b) ranges from 70 000 g/mol to 170 000 g/mol.

The average molecular weight (Mn) may be determined by size exclusion chromatography, using polystyrene standard for calibration.

By "styrene block content" is meant the weight proportion of styrene moieties present in the polystyrene block(s), per total weight proportion of the copolymer.

The styrene block copolymer (a) (herein as "copolymer (a)") may have a styrene block content from about 10 to about 21%. For example, the polymer (a) may have a styrene block content of about 20% or less (from about 10 to about 20%), or of about 19% or less (from about 10 to about 19%), or of about 18% or less (from about 10 to about 18%).

The styrene block copolymer (b) (herein as "copolymer (b)") may have a styrene block content from about 22% to about 45%. For example, the polymer (b) may have a styrene block content from about 23% (from about 23 to about 45%), or from about 24% (from about 24 to about 45%), or from about 25% (from about 25 to about 45%).

The hardness Shore A of the styrene block copolymers is measured according to the standard method NF EN ISO 686 at 15 seconds.

The polymer (a) may have a hardness Shore A from about 15 to about 50, preferably from about 20 to about 50. The polymer (a) may have a hardness Shore A from about 15 to about 45, preferably from about 20 to about 45.

The polymer (b) may have a hardness Shore A of more than about 60, preferably of more than 60 to about 90.

The polymeric component may comprise, by total weight of the polymeric component, from about 35 to about 100% of copolymer (a) and from about 0 to about 65% of copolymer (b); preferably from about 45 to about 100% of copolymer (a) and from about 0 to about 55% of copolymer (b); more preferably from about 55 to about 100% of copolymer (a) and from about 0 to about 45% of copolymer (b). Alternatively, the polymeric component may comprise, by total weight of the polymeric component, from about 35 to about 45% of copolymer (a) and from about 55 to about 65% of copolymer (b). Alternatively, the polymeric component may comprise, by total weight of the polymeric component, from about 25 to about 35% of copolymer (a) and from about 65 to about 75% of copolymer (b).

In one embodiment, the polymeric component consists of at least one copolymer (a) and at least one copolymer (b). In this embodiment, the polymeric component is free of any styrene block copolymers other than the copolymers (a) and (b). The polymeric component may comprise, by total weight of the polymeric component, from about 25 to about 95% of copolymer (a) and from about 5 to about 75% of copolymer (b); preferably from about 35 to about 90% of copolymer (a) and from about 10 to about 65% of copolymer (b); more preferably from about 45 to about 85% of copolymer (a) and from about 15 to about 55% of copolymer (b). For example, the polymeric component may comprise from about 5 to about 10% of copolymer (a) and from about 90 to 95% of polymer (b), or from about 10 to about 15% of copolymer (a) and from about 85 to 90% of polymer (b), or from about 15 to about 20% of copolymer (a) and from about 80 to 85% of polymer (b), or from about 20 to about 25% of copolymer (a) and from about 75 to 80% of polymer (b), or from about 25 to about 30% of copolymer (a) and from about 70 to 75% of polymer (b), or from about 30 to about 35% of copolymer (a) and from about 65 to 70% of polymer (b), or from about 35 to about 40% of copolymer (a) and from about 60 to 65% of polymer (b), or from about 40 to about 45% of copolymer (a) and from about 55 to 60% of polymer (b), or from about 45 to about 50% of copolymer (a) and from about 50 to 55% of polymer (b), or from about 50 to about 55% of copolymer (a) and from about 45 to 50% of polymer (b), or from about 55 to about 60% of copolymer (a) and from about 40 to 45% of polymer (b), or from about 60 to about 65% of copolymer (a) and from about 35 to 40% of polymer (b), or from about 65 to about 70% of copolymer (a) and from about 30 to 35% of polymer (b), or from about 70 to about 75% of copolymer (a) and from about 25 to 30% of polymer (b), or from about 75 to about 80% of copolymer (a) and from about 20 to 25% of polymer (b), or from about 80 to about 85% of copolymer (a) and from about 15 to 20% of polymer (b), or from about 85 to about 90% of copolymer (a) and from about 10 to 15% of polymer (b); or from about 90 to about 95% of copolymer (a) and from about 5 to 10% of polymer (b).

In an alternative embodiment, the polymeric component consists of at least one copolymer (a) i.e. about 100% of at least one copolymer (a). In this embodiment, the polymeric component is free of any styrene block copolymers, including the copolymer (b), other than the copolymer (a).

The copolymer (a) may be chosen from the group consisting of SB, SI, SEB, SEP, SBBS, SBS, SEBS, SEPS, SEEPS, SIBS, SIS, random-block SBR, random-block SIR, and mixtures thereof; preferably from the group consisting of SBBS, SBS, SEBS, SEPS, SEEPS, SIBS, SIS, random-block SBR, random-block SIR, and mixtures thereof; more preferably from the group consisting of SIS, random-block SBR, SEBS, and mixtures thereof, and even more preferably from the group consisting of SIS, random-block SBR, and mixtures thereof. Suitable copolymers (a) are commercially available under the tradenames Kraton® D1161 (SIS, styrene block content of about 15%, diblock content of about 19%, hardness Shore A of about 31) from Kraton Corporation, Vector® 4114A (SIS, styrene block content of about 15%, diblock content of about 42%, hardness Shore A of about 27) from TSRC Corporation, Sinopec® 1126 (SIS, styrene block content of about 16%, diblock content of about 50%, hardness Shore A of about 28) from Sinopec, Solprene® 1205 (random-block SBR, styrene block content of about 17.5%, random styrene content of about 7.5%, hardness Shore A of about 27) from Dynasol Group, Europrene® 1205 (random-block SBR, styrene block content of about 18%, random styrene content of about 7%, hardness Shore A of about 27) from Versalis (Eni), Sinopec® 2605 (random-block SBR, styrene block content of about 18%, random styrene content of about 7%, hardness Shore A of about 27) from Sinopec, JH8161 (SIS, styrene block content of about 16%, diblock content of about 50%, hardness Shore A of about 25) from Ningbo Jinhai Chenguang Chemical Corporation and Kraton® G1657 (SEBS, styrene block content of about 13%, diblock content of about 30%, hardness Shore A of about 47) from Kraton Corporation.

The copolymer (b) may be chosen from the group consisting of SB, SI, SEB, SEP, SBBS, SBS, SEBS, SEPS, SEEPS, SIBS, SIS, random-block SBR, random-block SIR, and mixtures thereof; preferably from SBBS, SBS, SEBS, SEPS, SEEPS, SIBS, SIS, random-block SBR, random-block SIR, and mixtures thereof; more preferably from the group consisting of SIS, SBS, SEBS and mixtures thereof. Suitable copolymers (b) are commercially available under the tradenames Quintac® 3280 (SIS, styrene block content of about 25%, diblock content of about 17%, hardness Shore A of about 61) from Zeon Corporation, Europrene® SOL TE9326 (SIS, styrene block content of about 30%, diblock content of about 15%, hardness Shore A of about 61) from Polimeri Europa (Eni), Europrene® SOL T166 (SBS, styrene block content of about 30%, diblock content of about 10%, hardness Shore A of about 72) from Versalis (Eni), Taipol® 6153 (SEBS, styrene block content of about 29%, diblock content of about 0%, hardness Shore A of about 79) from TSRC Corporation, Kraton® G1726 (SEBS, styrene block content of about 30%, diblock content of about 70%, hardness Shore A of about 77) from Kraton Corporation.

In an embodiment, the hot melt composition (the polymeric composition) is substantially free of radial styrene block copolymers.

In one embodiment, the polymeric component comprises, more preferably consists of, by total weight of the polymeric component:

- from about 25 to about 100% by weight of at least one linear styrene block copolymer (a) having a styrene block content of about 21% or less and a hardness Shore A of about 45 or less;
- from about 0 to about 75% by weight of at least one linear styrene block copolymer (b) having a styrene block content from about 22% to about 45%;

the copolymer (a) being chosen from the group consisting of SIS, random-block SBR and mixtures thereof.

In one embodiment, the polymeric component comprises, more preferably consists of, by total weight of the polymeric component:

- from about 25 to about 100% by weight of at least one linear styrene block copolymer (a) having a styrene block content of about 21% or less and a hardness Shore A of about 45 or less;
- from about 0 to about 75% by weight of at least one linear styrene block copolymer (b) having a styrene block content from about 22% to about 45%;

the copolymer (a) being chosen from the group consisting of SB, SI, SEB, SEP, SBBS, SBS, SEBS, SEPS, SEEPS, SIBS, SIS, random-block SBR, random-block SIR, and mixtures thereof;

at least one of the copolymer(s) (a) being a random-block SBR. Preferably, the content of random-block SBR in the hot melt composition is less than 11 wt %, more preferably less than 7 wt % based on the total weight of the hot melt composition.

For example, the hot melt composition may comprise the following polymeric compositions:

- from about 60 to about 70% of random-block SBR copolymer (a) and from about 30 to about 40% of SIS copolymer (b);
- from about 75 to about 85% of random-block SBR copolymer (a) and from about 15 to about 25% of SIS copolymer (b);
- from about 30 to about 40% of random-block SBR copolymer (a) and from about 60 to about 70% of SIS copolymer (b);
- from about 45 to about 55% of random-block SBR copolymer (a) and about 45 to about 55% of SIS copolymer (b);
- from about 20 to about 30% of random-block SBR copolymer (a) and from about 70 to about 80% of SIS copolymer (b);
- from about 60 to about 70% of random-block SBR copolymer (a) and from about 30 to about 40% of SEBS copolymer (b);
- from about 60 to about 70% of SIS copolymer (a) and from about 30 to about 40% of SIS copolymer (b);
- from about 60 to about 70% of SIS copolymer (a) and from about 30 to about 40% of SEBS copolymer (b);
- from about 100% of SIS copolymer (a);
- from about 100% of random-block SBR polymer (a);
- from about 100% of a composition of copolymers (a) consisting of about 60 to about 70% of SIS copolymer (a) and from about 30 to about 40% of random-block SBR copolymer (a);
- from about 100% of a composition of copolymers (a) consisting of about 45 to about 55% of SIS copolymer (a) and from about 45 to about 55% of random-block SBR copolymer (a);
- from about 27 to about 37% of random-block SBR copolymer (a), from about 27 to about 37% of SIS copolymer (b) and from about 30 to about 40 of SEBS copolymer (b);
- from about 30 to about 40% of SIS copolymer (a), from about 17 to about 27% of SEBS copolymer (a) and from about 38 to about 48% of SIS copolymer (b).

Preferably, the hot melt composition comprises:

- from about 100% of a composition of copolymers (a) consisting of about 60 to about 70% of SIS copolymer (a) and from about 30 to about 40% of random-block SBR copolymer (a); or
- from about 100% of a composition of copolymers (a) consisting of about 45 to about 55% of SIS copolymer (a) and from about 45 to about 55% of random-block SBR copolymer (a).

In one embodiment, the styrene block polymeric component is free of hydrogenated styrene block copolymer.

Hydrogenated styrene block copolymers are well known. It can be SEBS, SEB, SEP, SEPS, SBS, SBBS, SEEPS, SIBS.

In a preferred embodiment, the hot melt adhesive composition does not comprise propylene-based polymer such as for example propylene-ethylene copolymer. Example of propylene-ethylene copolymer may be Vistamaxx 6202 from ExxonMobil.

The hot melt adhesive composition may have a Brookfield viscosity at 163° C. from about 500 to about 8,000 mPa·s; preferably from about 500 to about 4,000 mPa·s, more preferably from about 800 to about 3,000 MPa·s. The Brookfield viscosity is measured according to the standard method ASTM method D-3236, using a Brookfield viscometer of the type Spindle 27, at a temperature of about 163° C.

The hot melt composition may have an average peel performance on Lyocell fibers from at least about 0.236 N/cm (0.6 N/inch), preferably from 0.236 N/cm (0.6 N/inch) to 1.181 N/cm (3 N/inch), more preferably from 0.236 N/cm (0.6 N/inch) to 0.984 N/cm (2.5 N/inch). For example, the composition may have an average peel performance on Lyocell fibers of at least about 0.276 N/cm (0.7 N/inch), or at least about 0.315 N/cm (0.8 N/inch), or at least about 0.354 N/cm (0.9 N/inch), or at least about 0.394 N/cm (1.0 N/inch). The peel performance on Lyocell fibers is measured according to the method entitled "pad attachment method" described below. While the hot melt composition may be used as an adhesive on a large variety of substrates, and in particular fabrics, the inventors have shown that this composition was particularly suitable for use as an adhesive on eucalyptus-based Lyocell fibers, contrary to conventional hot melt compositions, including compositions comprising a polymeric component consisting of at least one linear styrene block copolymer (b) having a styrene block content from about 22% and a hardness Shore A of more than about 60.

Tackifying Resin

The hot melt adhesive composition comprises a tackifying resin (tackifier). The hot melt adhesive composition comprises from about 40 to about 65%, preferably from about 45 to about 60%, more preferably from about 50 to about 55%, by weight of a tackifying resin relative to the total weight of the composition.

Suitable tackifying resins are those which are compatible with the polymeric component, which extend adhesive properties and which improve specific adhesion. As used herein, the term "tackifying resin" include:

- Aliphatic petroleum hydrocarbon resins, resulting from the polymerization of monomers consisting primarily of olefins and di-olefins, and their hydrogenated derivatives thereof;
- Cyclic petroleum hydrocarbon resins and their hydrogenated derivatives thereof;
- Aromatic petroleum hydrocarbon resins and their hydrogenated derivatives thereof;
- Aromatic-modified cycloaliphatic resins and the hydrogenated derivatives thereof;
- Polyterpene resins, generally resulting from the polymerization of terpene hydrocarbons (e.g. the mono-terpene known as pinene), in the presence of Friedel-Crafts catalysts at moderately low temperatures, and their hydrogenated derivatives;
- Copolymers and terpolymers of natural terpenes (e.g. styrene/terpene, α-methyl styrene/terpene and vinyl toluene/terpene);
- Natural and modified rosin (e.g. gum rosin, wood rosin, tall-oil rosin, distilled rosin, hydrogenated rosin, dimerized rosin, polymerized rosin, rosin esters and their hydrogenated derivatives);

Glycerol and pentaerythritol esters of natural and modified rosin (e.g. the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall-oil rosin, and the phenolic modified pentaerythritol ester of rosin); and, Phenolic-modified terpene resins (e.g. the resin product resulting from the condensation in an acidic medium of a terpene and a phenol).

In one embodiment, the hot melt adhesive composition comprises a tackifying resin (a) being aliphatic petroleum hydrocarbon resins, resulting from the polymerization of monomers consisting primarily of olefins and di-olefins, and their hydrogenated derivatives thereof. The aliphatic petroleum hydrocarbon resins, and their hydrogenated derivates thereof, may be based on C5 olefins, C9 olefins, di-cyclopentadiene (DCPD) and their mixtures thereof. Suitable tackifying resins are commercially available under the tradenames Eastotac® H100W (resin C5 fully hydrogenated) from Eastman Chemical Company; Escorez® 2203LC (resin C5/C9) from ExxonMobil Chemical company; Sukorez® SU 120 (resin DCPD fully hydrogenated), Sukorez® SU 210 (resin DCPD/C5 fully hydrogenated), Sukorez® SU 420 (resin DCPD/C9 partially hydrogenated) and Sukorez® SU525 (resin DCPD fully hydrogenated) from Kolon; Regalite® S7125 (resin C9 partially hydrogenated) from Eastman Chemical Company; HS-130 (resin DCPD hydrogenated) from Hanwha Solutions/chemical Corporation; Luhorez HD1120 (resin DCPD hydrogenated) from Tianjin Luhua Chemical, Eastotac® H100W (resin C5 fully hydrogenated) from Eastman and Regalite® S7125 (C9 partially hydrogenated) from Eastman, Henghe HM1000 (resin DCPD/C9 (3%) hydrogenated) from Henghe Materials and Science Technology Co. LTD and Henghe H5-1001 (resin C5 fully hydrogenated) from Henghe Materials and Science Technology Co. LTD.

In another embodiment, the hot melt adhesive composition comprises a tackifying resin (b) consisting of a natural and modified rosin and their hydrogenated rosin. Suitable tackifying resins are commercially available under the tradename Foral® DX (rosin resin fully hydrogenated) from DRT and Foral® AX-E (rosin resin fully hydrogenated) from Eastman.

In another embodiment, the hot melt adhesive composition comprises a tackifying resin consisting of a mixture of a tackifying resin (a) and a tackifying resin (b), as described above; preferably a tackifying resin consisting of from about 57% to about 77% of a tackifying resin (a) and from about 23 to about 43% of a tackifying resin (b), by total weight of the composition; more preferably a tackifying resin consisting of from about 62% to about 72% of a tackifying resin (a) and from about 28 to about 38% of a tackifying resin (b), by total weight of the composition.

The tackifying resin may have a Ring and Ball softening point (measured by ASTM E28) from about 50° C. to about 140° C.

Plasticizer

The hot melt adhesive composition of the present invention comprises a plasticizer. The plasticizer may be a solid or a liquid plasticizer.

The hot melt adhesive composition comprises from about 15 to about 40%, preferably from about 20 to about 35%, more preferably from about 25 to about 30%, by weight of a plasticizer relative to the total weight of the composition.

The plasticizer may be chosen from the group consisting of naphthenic and paraffinic oils, olefin oligomers, low molecular weight polymers, glycol benzoates, vegetable and animal oils, and derivatives thereof.

The plasticizer may confer good processability to the hot melt adhesive composition. Moreover, the plasticizer may also provide desired viscosity control without substantially decreasing the adhesive strength or the service temperature (temperature of use) of the hot melt adhesive.

Naphthenic oils and paraffinic oils are petroleum-based oils which consist in a mixture of naphthenic hydrocarbons (e.g. aliphatic, saturated or unsaturated, C4 to C7-member hydrocarbon rings; preferably aliphatic, saturated or unsaturated, C4 to C6-member rings, including cycloalkanes such as cyclopentane, cyclohexane, cycloheptane), paraffinic hydrocarbons (saturated, linear or branched, alkanes) and aromatic hydrocarbons (aromatic hydrocarbon rings, which may be monocyclic or polycyclic, and preferably aromatic C6-member hydrocarbon rings).

The classification of naphthenic and paraffinic oil is made based on the amount of each type of hydrocarbons in the oil. Typically, paraffinic oils have a paraffinic hydrocarbons content of at least about 50% by weight; naphthenic oils have a naphthenic hydrocarbons content from about 30% to about 40% by weight, relative to the total weight of the plasticizer.

In a preferred embodiment, the plasticizer is a paraffinic oil.

Suitable plasticizers are commercially available under the tradenames Nyflex® 223 and Nyflex® 222B (naphtenic oils) from Nynas, Parol® (paraffinic oils), Kaydol® (paraffinic oil) from Sonneborn, Olympus® L500 from Ergon, Primol® 352 and 382 from Exxon Mobil, Calsol® 5550 from Calumet and Karamay N4010 (naphtenic oils) from Petrochina Karamay Petrochemical Co. LTD.

The oligomers may be selected from the group consisting of polypropylene, polybutene, hydrogenated polyisoprene, hydrogenated butadiene, or the like having average molecular weights between about 100 and about 10,000 g/mol.

The vegetable and animal oils may be selected from glycerol esters of usual fatty acids and polymerization products thereof.

Stabilizers (Antioxidants)

The hot melt adhesive composition also preferably comprises at least one stabilizer (antioxidant).

The hot melt adhesive composition comprises from about 0 to about 5%, preferably from 0 to about 3%, more preferably from about 0.1 to about 3%, more preferably from about 0.1 to 2%, by weight of a stabilizer, by total weight of the composition.

Suitable stabilizers are incorporated to help protect the polymers noted above, and thereby the total adhesive system from the effects of thermal and oxidative degradation which normally occurs during the manufacture and application of the adhesive, as well as in the ordinary exposure of the final product to the ambient environment. Such degradation is usually manifested by deterioration in the appearance, physical properties and performance characteristics of the hot melt adhesive composition.

Among the applicable stabilizers are high molecular weight hindered phenols and multifunction phenols, such as sulfur and phosphorous-containing phenols. Hindered phenols are well known to those skilled in the art and may be characterized as phenolic compounds that also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include: 1,3,5-trimethyl-2,4,6-tris(3-5-di-tert-butyl-4-hydroxybenzyl) benzene; pentaerythritol tetrakis-3(3,5-di-tert-butyl-4-hydroxyphenyl) propionate; n-octadecyl-3(3,5-di-tert-butyl-4-hydroxyphenyl) propionate, 4.4'-methylenebis(4-methyl-6-tert-butylphenol); 2,6-di-tert-butylphenol; 6-(4-hydroxyphenoxy)-2,4-bis(n-octylthio)-1,3,5-triazine; 2,3,6-tris(4-hydroxy-3,5-di-tert-butyl-phenoxy)-1,3,5-triazine; di-n-octadecyl-3,5-di-tert-butyl-4-hydroxybenzylphosphonate; 2-(n-octyl-thio)ethyl-3,5-di-tert-butyl-4-hydroxybenzoate and sorbitol hexa-3(3,5-di-tert-butyl-4-hydroxy-phenyl)propionate.

The performance of these stabilizers may be further enhanced by utilizing, in conjunction therewith; (1) synergists such as, for example, thiodipropionate esters and phosphites; examples of these include dialuryl thiodipropionate (DLTDP) and tris(nonylphenyl)phosphite (TNPP), respectively; and (2) chelating agents and metal deactivators as, for example, ethylenediaminetetraacitic acid, salts thereof and disalicylalpropylenediimine.

Suitable antioxidants are commercially available under the tradenames Irganox® 1010 (tetrakis(methylene(3,5-di-ter-butyl-4-hydroxyhydrocinnamate)) methane), Irgafos® 168 (tris(2,4-ditert-butylphenyl)phosphate) from BASF, and Chinox® 1010 (pentaerythritol tetrakis(3-(3,5-di-tert-butyl-4-hydroxyphenyl) propionate)) from Shuangjian, Evernox® 1010 and Everfos® 168 from Everspring Chemical, Songnox® 10 and 1680 from Songwon.

Other Additives

The hot melt adhesive composition may further comprise at least one additive, preferably in an amount of from 0 to 5%, by total weight of the composition.

The hot melt adhesive composition may further comprise at least one wax. The hot melt adhesive composition may comprise from about 0 to about 5%, preferably from about 0 to about 3%, by weight of wax, by total weight of the composition. In one embodiment, the hot melt adhesive composition may comprise from about 0.1 to about 5%, preferably from about 0.1 to about 3%, by weight of wax, by total weight of the composition. Alternatively, the hot melt adhesive composition may be free of wax. The presence of the wax makes it possible to reduce the melt viscosity of the hot melt adhesive without appreciably decreasing its adhesive bonding characteristics. These waxes are also used to reduce the open time, or set-up time of the composition without affecting the temperature performance.

The hot melt adhesive composition may comprise further additives, selected from the group consisting of inert colorants (e.g. titanium dioxide), fillers (e.g. talc, calcium carbonate, clay, silica, mica, wollastonite, feldspar, aluminum silicate, alumina, hydrated alumina, glass microspheres, ceramic microspheres, thermoplastic microspheres and mixtures thereof), surfactants, additional polymers other than styrene block copolymers, crosslinking agents, nucleating agents, reactive compounds, fire-retardant mineral or organic agents, ultraviolet (UV) or infrared (IR) light absorbing agents, and UV or IR fluorescing agents. These optional auxiliary additives are well known in this art.

The additional polymers may be chosen from the group consisting of polyolefins, amorphous poly-alpha-olefins, ethyl-vinyl-acetate polymers (EVA), polyamides, and mixtures therefor. The hot melt adhesive may comprise from about 0 to about 5% by weight of at least one additional polymer, by total weight of the composition.

Use

In a second aspect, the present invention relates to the use of the hot melt adhesive compositions as described above, for adhering a hygiene disposable article on a fabric.

The hygiene disposable article may be chosen from nonwoven hygiene disposable articles; preferably from the group consisting of disposable diapers, training pants, adult incontinent products (pads or briefs), feminine care products (napkins or pads) and surgical masks; more preferably from adult incontinent products (pads or briefs) and feminine care products (napkins or pads).

The fabric may be manufactured utilizing natural or synthetic fibers, including cotton, nylon, polyester, other man-made fibers and mixtures thereof.

In a preferred embodiment, the fabrics are manufactured utilizing Lyocell fibers, more preferably eucalyptus based Lyocell fibers. Hence, the present invention particularly relates to the use of the hot melt composition as described above for adhering a hygiene disposable articles, particularly an incontinent product (pads or briefs) or a feminine care product (napkins or pads), on a fabric made from Lyocell fibers, preferably eucalyptus-based Lyocell fibers. By "Lyocell fibers" (also known as "fibers of the Lyocell genus" or "solvent-spun fibers") is meant fibers obtained by a solvent-spinning process, wherein the cellulose is dissolved directly in an aqueous tertiary amine-oxide without the formation of a derivative, and the solution is spun or wherein the cellulose fibers are produced by dissolving cellulose in an organic solvent without the formation of a derivative and extruding fibers from said solution by means of a dry-wet spinning process or a melt-blown process. Lyocell is a generic name allocated by BISFA (The International Bureau for the Standardization of manmade fibers).

Lyocell fibers are conventional fibers known in the art. Suitable processes for producing Lyocell fibers are described for example in the U.S. Pat. No. 4,246,221 published on 20 Jan. 1981, the PCT application WO 2018/104330 A1 published on 14 Jun. 2018 and the PCT application WO 2009/036481 A1 published on 26 published March 2009, which are incorporated herewith by reference.

Generally, in the Lyocell process wood is chipped and digested chemically, to remove the lignin and to soften them enough to be mechanically milled to a wet pulp. This pulp may be bleached. Then, it is dried into a continuous sheet and rolled onto spools. Tertiary amine N-oxides such as N-methylmorpholine N-oxide are most often used as a solvent in the Lyocell Process alone or together with water. Other solvents such as N-methylpiperidine-N-oxide, N-methylpyrrolidone-oxide, and dimethylcyclohexylamine oxide can also be used. The pulp is dissolved in N-oxide solvent, giving a solution called "dope". During this step, cellulose is impregnated with the tertiary N-oxide solvent. The cellulose solution is then shaped by extrusion or by spinning into air. More particularly, this solution is pumped through spinnerets, devices used with a variety of manmade fibers. The spinneret is pierced with small holes rather like a showerhead; when the solution is forced through it, continuous strands of filament come out. The fibers are drawn in air to align the cellulose molecules, imparting the Lyocell fibers improved physical properties such as its characteristic high strength. The fibers are then immersed in another solution of amine oxide, diluted this time, which sets the fiber strands. Then they are washed with de-mineralized water. The Lyocell fiber next passes to a drying area, where the water is evaporated from it. The strands then pass to a finishing area, where a lubricant, which may be a soap or silicone or other agent depending on the future use of the fiber, is applied. This step is basically a detangler, prior to carding and spinning into yarn. The dried, finished fibers are at this stage in a form called tow, a large untwisted bundle of continuous lengths of filament. The bundles of tow are taken to a crimper, a machine that compresses the fiber, giving it texture and bulk. The crimped fiber is carded by mechanical carders, which perform an action like combing, to separate and order the strands. The carded strands are cut and baled for shipment to a fabric mill. The entire manufacturing process, from unrolling the raw cellulose to baling the fiber, takes about two hours. After this, the Lyocell may be processed in many ways. It may be spun with another fiber, such as cotton or wool. The resulting yarn can be woven or knitted like any other fabric, and may be given a variety of finishes, from soft and suede-like to silky.

Lyocell fibers have a high tensile strength, a high wet-modulus and a high loop strength.

EXAMPLES

The following examples illustrate the invention without limiting it.

The following materials were used:

Plasticizer 1: Nyflex® 223 (naphtenic oils) from Nynas;

Plasticizer 2: Parol® (paraffinic oils) from Sonneborn;

Plasticizer 3: Karamay N4010 (naphtenic oils) from Petrochina Karamay Petrochemical Co. LTD;

Resin 1: Foral® DX (rosin resin fully hydrogenated) from DRT;

Resin 2: Sukorez® SU 210 (resin DCPD/C5 fully hydrogenated) from Kolon;

Resin 3: Sukorez® SU 420 (resin DCPD/C9 partially hydrogenated from Kolon;

Resin 4: Hanwha HS-130 (resin DCPD hydrogenated) from Hanwha Solutions/chemical Corporation;

Resin 5: Henghe HM1000 (resin DCPD/C9 (3%) hydrogenated) from Henghe Materials and Science Technology Co. LTD;

Resin 6: Henghe H5-1001 (resin C5 fully hydrogenated) from Henghe Materials and Science Technology Co. LTD;

Polymer (a1): Sinopec® 1126 (SIS, styrene block content of about 16%, diblock content of about 50%, hardness Shore A of about 28) from Sinopec;

Polymer (a2): Solprene® 1205 (random-block SBR, styrene block content of about 17.5%, random styrene content of about 7.5%, hardness Shore A of about 27) from Dynasol Group;

Polymer (a3): JH8161 (SIS, styrene block content of about 16%, diblock content of about 50%, hardness Shore A of about 25) from Ningbo Jinhai Chenguang Chemical Corporation;

Polymer (a4): Kraton® G1657 (SEBS, styrene block content of about 13%, diblock content of about 30%, hardness Shore A of about 47) from Kraton Corporation;

Polymer (b1): Quintac® 3280 (SIS, styrene block content of about 25%, diblock content of about 17%, hardness Shore A of about 61) from Zeon Corporation;

Polymer (b2): Europrene® SOL TE9326 (SIS, styrene block content of about 30%, diblock content of about 15%, hardness Shore A of about 61) from Polimeri Europa (Eni);

Polymer (b3): Kraton® G1726 (SEBS, styrene block content of about 30%, diblock content of about 70%, hardness Shore A of about 77) from Kraton Corporation;

Antioxidant: Irganox® 1010 (tetrakis(methylene(3,5-di-ter-butyl-4-hydroxyhydrocinnamate))methane) from BASF.

Average Hardness Shore A (Polymeric Component)

The average hardness shore A is calculated as follows: the sum of [the hardness Shore A of each copolymer multiplied by its weight proportion in the polymeric component], divided by 100.

Brookfield Viscosity

The Brookfield viscosity is measured according to the standard method ASTM method D-3236, using a Brookfield viscometer of the type Spindle 27, at a temperature of about 163° C.

Peel Performance

The peel performance is measured according to the below method entitled "pad attachment method".

Equipment: table coater;

Pad materials: a first substrate being a release liner and a second substrate being either a polyethylene non breathable back-sheet or a cloth-like back-sheet (non-woven) are assembled with the pressure sensitive hot melt adhesive using a table coater.

Undergarment material: undergarment comprising from about 80 to about 85% eucalyptus based Lyocell fibers;

Application of the adhesive: The adhesive is applied on the first substrate (release liner) with a slot pattern at a temperature of about 150° C., an add-on of about 25 gsm, a speed of coating being between 14 m/min and 100 m/min, and a compression over the second substrate of $10^8$ mPa. Laminates are shelved for a minimum of 24 h at 23° C. before testing.

Test execution:

- cutting the laminate with a width of about 2.54 cm (1 inch) and a length of about 15 cm;
- washing the undergarment three times at 40° C. before testing;
- removing the first substrate (release liner) and applying the undergarment on the second substrate (back-sheet) on the adhesive side; and
- applying a roller of 0.6 kg back and forth at a speed of 1,500 mm/min;
- peeling the sample at 500 mm/min using a dynamometer (6 measurements);
- calculating the average peel performance from the six measurements, and comparing with the average peel performance of the reference composition.

Exemplified Compositions

| | C1 (ref) | C2 | C3 | C4 | C5 |
|---|---|---|---|---|---|
| Plasticizer 1 | 27.1 | — | 27.1 | — | — |
| Plasticizer 2 | — | 27.1 | — | 27.1 | — |
| Plasticizer 3 | — | — | — | — | 28 |
| Resin 1 | — | — | — | 17.2 | — |
| Resin 2 | 17.2 | — | 17.2 | — | — |
| Resin 3 | 34.9 | — | 34.9 | 34.9 | — |
| Resin 4 | — | 52.1 | — | — | — |
| Resin 5 | — | — | — | — | 14 |
| Resin 6 | — | — | — | — | 34 |
| Polymer (a1) | — | 10.2 | 20.4 | — | — |
| Polymer (a2) | — | 10.2 | — | 6.6 | — |
| Polymer (a3) | — | — | — | — | 8 |
| Polymer (a4) | — | — | — | — | 5 |
| Polymer (b1) | 13.2 | — | — | 6.6 | 10 |
| Polymer (b2) | 7.2 | — | — | — | — |
| Polymer (b3) | — | — | — | 7.2 | — |
| Antioxidant | 0.4 | 0.4 | 0.4 | 0.4 | 1 |
| Total (%) | 100 | 100 | 100 | 100 | 100 |
| Average hardness Shore A | 61 | 29 | 28 | 56 | 45 |
| Brookfield viscosity at 163° C. (mPa · s) | 1083 | 1661 | 1765 | 634 | ND |
| Peel performance increase vs reference | — | +171% | +169% | +68% | ND |

ND = not determined

Contrary to the composition of reference C1, the compositions according to the present invention C2, C3 and C4 show a satisfactory peel performance on eucalyptus based Lyocell fibers and achieve improved adhesion of nonwoven hygiene disposable articles on fabrics.

The invention claimed is:

1. A hot melt adhesive composition comprising, by total weight of the composition:

from 5 to 35% by weight of at least one styrene block polymeric component having an average hardness Shore A of 60 or less, wherein the at least one styrene block polymeric component comprises at least one linear styrene block copolymer (a) and at least one linear styrene block copolymer (b), wherein the at least one linear styrene block copolymer (a) is selected from the group consisting of SB, SI, SEB, SEP, SBBS, SBS, SEBS, SEPS, SEEPS, SIBS, SIS, random-block SBR, random-block SIR, and mixtures thereof and the at least one linear styrene block copolymer (b) is selected from the group consisting of SB, SI, SEB, SEP, SBBS, SBS, SEBS, SEPS, SEEPS, SIBS, SIS, random-block SBR, random-block SIR, and mixtures thereof, and wherein the at least one styrene block polymeric component is selected from the group consisting of:

from 60 to 70% of random-block SBR copolymer (a) and from 30 to 40% of SIS copolymer (b);

from 75 to 85% of random-block SBR copolymer (a) and from 15 to 25% of SIS copolymer (b);

from 45 to 55% of random-block SBR copolymer (a) and 45 to 55% of SIS copolymer (b);

from 20 to 30% of random-block SBR copolymer (a) and from 70 to 80% of SIS copolymer (b);

from 60 to 70% of random-block SBR copolymer (a) and from 30 to 40% of SEBS copolymer (b);

from 60 to 70% of SIS copolymer (a) and from 30 to 40% of SIS copolymer (b);

from 60 to 70% of SIS copolymer (a) and from 30 to 40% of SEBS copolymer (b);

100% of SIS copolymer (a);

100% of random-block SBR polymer (a);

100% of a composition of copolymers (a) consisting of 60 to 70% of SIS copolymer (a) and from 30 to 40% of random-block SBR copolymer (a);

100% of a composition of copolymers (a) consisting of 45 to 55% of SIS copolymer (a) and from 45 to 55% of random-block SBR copolymer (a); and from 27 to 37% of random-block SBR copolymer (a), from 27 to 37% of SIS copolymer (b) and from 30 to 40% of SEBS copolymer (b);

from 40 to 65% by weight of at least one tackifying resin;

from 15 to 40% by weight of at least one plasticizer;

from 0 to 5% by weight of at least one stabilizer; wherein the composition does not comprise a propylene-based polymer.

2. The hot melt adhesive composition, according to claim 1, wherein the at least one styrene block polymeric component has an average hardness Shore A of 50 or less.

3. The hot melt adhesive composition, according to claim 1, wherein the at least one stabilizer is in an amount of from 0 to 3% by weight, the hot melt adhesive composition further comprising from 0 to 5% of at least one additive, by total weight of the composition.

4. The hot melt adhesive composition, according to claim 1, wherein the average molecular weight (Mn) of each of the at least one linear styrene block copolymer(s) (a) and the at least one linear styrene block copolymer(s) (b) ranges from 70 000 g/mol to 170 000 g/mol.

5. The hot melt adhesive composition, according to claim 1, wherein the polymeric component comprises, by total weight of the polymeric component, from 35 to 100% of the at least one linear styrene block copolymer (a) and from 0 to 65% of the at least one linear styrene block copolymer (b).

6. The hot melt adhesive composition, according to claim 1, wherein the polymeric component comprises, by total weight of the polymeric component, from 25 to 95% of the at least one linear styrene block copolymer (a) and from 5 to 75% of the at least one linear styrene block copolymer (b).

7. The hot melt adhesive composition, according to claim 1, wherein the polymeric component consists of at least one of the at least one linear styrene block copolymer (a).

8. The hot melt adhesive composition, according to claim 1, wherein at least one of the at least one linear styrene block copolymer(s) (a) is a random-block SBR.

9. The hot melt adhesive composition, according to claim 1, wherein the composition has a Brookfield viscosity at 163° C. from 500 to 8,000 mPa·s.

10. Method of adhering a hygiene disposable article on a fabric comprising using the hot melt adhesive composition according to claim 1.

11. The method of claim 10, wherein the hygiene disposable article is chosen from nonwoven hygiene disposable articles.

12. The method of claim 10, wherein the fabric is manufactured utilizing natural or synthetic fibers.

* * * * *